(12) United States Patent
Campbell et al.

(10) Patent No.: US 11,786,709 B2
(45) Date of Patent: Oct. 17, 2023

(54) EXPANDABLE MEDICAL DEVICES

(71) Applicant: W. L. Gore & Associates, Inc., Newark, DE (US)

(72) Inventors: Carey V. Campbell, Flagstaff, AZ (US); Cody L. Hartman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 434 days.

(21) Appl. No.: 16/991,618

(22) Filed: Aug. 12, 2020

(65) Prior Publication Data

US 2020/0368503 A1   Nov. 26, 2020

Related U.S. Application Data

(63) Continuation of application No. 15/146,047, filed on May 4, 2016, which is a continuation of application No. 13/183,163, filed on Jul. 14, 2011, now Pat. No. 9,370,647.

(51) Int. Cl.
| | | |
|---|---|---|
| *A61M 25/10* | (2013.01) | |
| *A61L 29/04* | (2006.01) | |
| *A61L 29/14* | (2006.01) | |
| *A61B 17/22* | (2006.01) | |
| *A61F 2/958* | (2013.01) | |

(52) U.S. Cl.
CPC ........... *A61M 25/104* (2013.01); *A61B 17/22* (2013.01); *A61L 29/041* (2013.01); *A61L 29/146* (2013.01); *A61B 2017/22001* (2013.01); *A61B 2017/22051* (2013.01); *A61B 2017/22081* (2013.01); *A61F 2/958* (2013.01); *A61M 2025/1081* (2013.01); *A61M 2025/1084* (2013.01)

(58) Field of Classification Search
CPC ........ A61M 25/104; A61M 2025/1081; A61M 2025/1084; A61B 17/22; A61B 2017/22001; A61B 2017/22051; A61L 29/041; A61L 29/146; A61F 2/958
See application file for complete search history.

(56) References Cited

U.S. PATENT DOCUMENTS

| | | |
|---|---|---|
| 5,308,664 A | 5/1994 | House et al. |
| 5,409,495 A | 4/1995 | Osborn |
| 5,470,313 A | 11/1995 | Crocker et al. |
| 5,512,051 A | 4/1996 | Wang et al. |
| 5,545,209 A | 8/1996 | Roberts et al. |
| 5,738,653 A | 4/1998 | Pinchuk et al. |
| 5,743,876 A | 4/1998 | Swanson |
| 5,747,128 A | 5/1998 | Campbell et al. |
| 5,843,116 A | 12/1998 | Crocker et al. |
| 6,120,477 A | 9/2000 | Campbell et al. |
| 6,120,523 A | 9/2000 | Crocker et al. |
| 6,200,290 B1 | 3/2001 | Burgmeier |
| 6,328,710 B1 | 12/2001 | Wang et al. |

(Continued)

FOREIGN PATENT DOCUMENTS

| | | |
|---|---|---|
| CN | 1391452 A | 1/2003 |
| DE | 102005007596 A1 | 8/2006 |

(Continued)

*Primary Examiner* — Thomas McEvoy

(57) ABSTRACT

A medical device with an expandable element and expandable tubular sleeve surrounding at least a portion of the expandable element which influences the rate, shape and/or force required to expand the expandable element and methods for use in a body lumen are provided.

19 Claims, 3 Drawing Sheets

(56) References Cited

U.S. PATENT DOCUMENTS

| | | |
|---|---|---|
| 6,626,861 B1 | 9/2003 | Hart et al. |
| 6,676,693 B1 | 1/2004 | Belding et al. |
| 6,866,649 B2 | 3/2005 | Ferrera et al. |
| 6,872,223 B2 | 3/2005 | Roberts et al. |
| 6,890,395 B2 | 5/2005 | Simhambhatla |
| 7,048,713 B2 | 5/2006 | Wang |
| 7,163,523 B2 | 1/2007 | Devens et al. |
| 10,765,842 B2 | 9/2020 | Hartman et al. |
| 2002/0045914 A1 | 4/2002 | Roberts et al. |
| 2004/0024442 A1 | 2/2004 | Sowinski et al. |
| 2004/0073165 A1 | 4/2004 | Musbach et al. |
| 2004/0170782 A1 | 9/2004 | Wang et al. |
| 2004/0186502 A1 | 9/2004 | Sampson et al. |
| 2005/0089655 A1 | 4/2005 | Lim |
| 2006/0015064 A1 | 1/2006 | Kastenhofer |
| 2006/0178685 A1 | 8/2006 | Melsheimer |
| 2006/0190075 A1 | 8/2006 | Jordan et al. |
| 2006/0206189 A1 | 9/2006 | Furst et al. |
| 2006/0233991 A1 | 10/2006 | Humphrey et al. |
| 2006/0271093 A1 | 11/2006 | Holman et al. |
| 2008/0125707 A1 | 5/2008 | Wilson et al. |
| 2008/0171977 A1 | 7/2008 | Blix |
| 2009/0076446 A1 | 3/2009 | Dubuclet et al. |
| 2009/0076449 A1 | 3/2009 | Geis et al. |
| 2009/0112159 A1 | 4/2009 | Slattery et al. |
| 2009/0137954 A1 | 5/2009 | Kastenhofer |
| 2009/0163879 A1 | 6/2009 | Weber et al. |
| 2009/0171277 A1 | 7/2009 | Pepper |
| 2009/0227948 A1 | 9/2009 | Chen et al. |
| 2010/0022949 A1 | 1/2010 | Eidenschink |
| 2010/0191323 A1 | 7/2010 | Cox |
| 2010/0324584 A1 | 12/2010 | Shaw |
| 2016/0243340 A1 | 8/2016 | Campbell et al. |

FOREIGN PATENT DOCUMENTS

| | | |
|---|---|---|
| EP | 0313263 A2 | 4/1989 |
| JP | 63-077461 A | 4/1988 |
| JP | 02-000645 A | 1/1990 |
| JP | 2003-500152 A | 1/2003 |
| JP | 2010-537739 A | 12/2010 |
| WO | 2006/130194 A2 | 12/2006 |
| WO | 2010/064278 A1 | 6/2010 |
| WO | 2013/009740 A1 | 1/2013 |

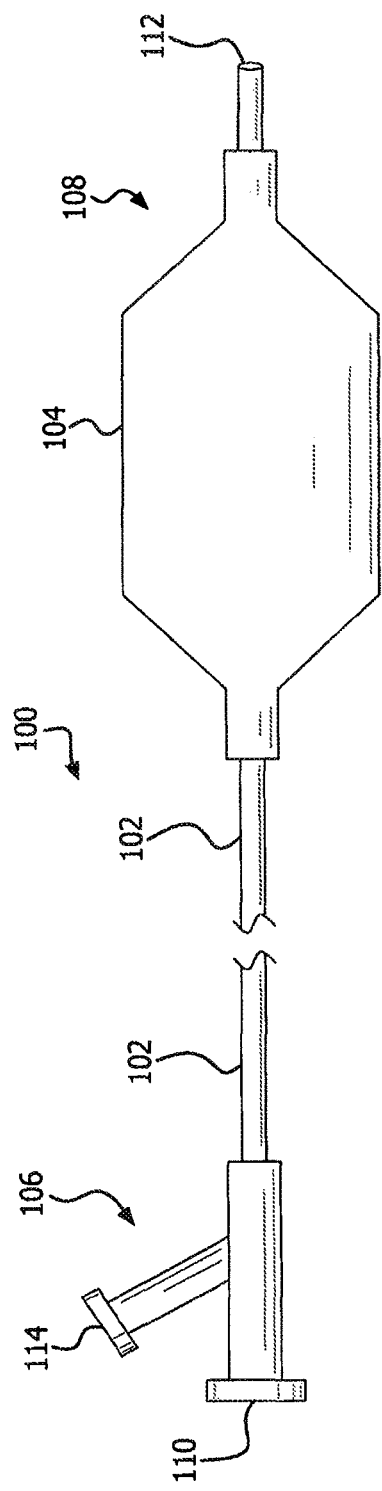
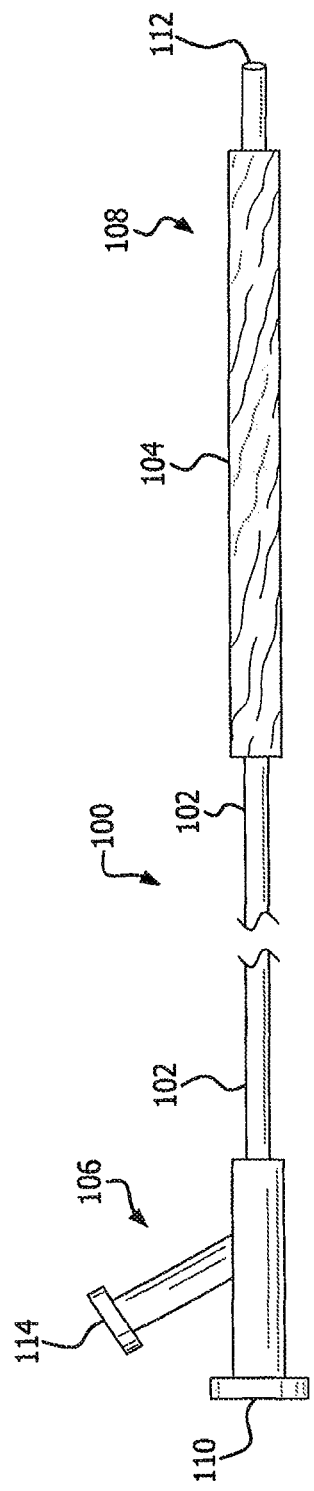
FIG. 1
FIG. 2

EXPANDABLE MEDICAL DEVICES

CROSS-REFERENCE TO RELATED APPLICATION

This application is a continuation of U.S. patent application Ser. No. 15/146,047, filed May 4, 2016, which is a continuation of U.S. patent application Ser. No. 13/183,163, filed Jul. 14, 2011, now U.S. Pat. No. 9,370,647, issued Jun. 21, 2016, both of which are incorporated herein by reference in their entireties for all purposes.

BACKGROUND OF THE INVENTION

Vascular dilatation balloons on medical devices generally fall into two classes. The first class of vascular dilatation balloons comprises a noncompliant balloon formed from a relatively nondistensible material such as polyethylene terephthalate (PET). Noncompliant balloons exhibit a substantially uniform exterior inflated profile which remains substantially unchanged upon increasing inflation pressures. Noncompliant balloons have been suggested to be advantageous because they allow the introduction of increased inflation pressure to break calcified lesions while retaining a predictable inflation profile thus minimizing damage to the surrounding lumen. Non-limiting examples of noncompliant balloons are disclosed in U.S. Pat. No. 6,200,290 to Burgmeier and Published Application U.S. 2010/0022949 to Eidenschink. Additional examples are commonly known in the art.

The second class of vascular dilatation balloons comprises compliant balloons. Compliant balloons expand in diameter upon increased inflation pressure. A problem with compliant balloons has been that upon inflation within a lesion, the balloon inflates unevenly around the plaque to form an hour glass type shape. The uneven inflation of the compliant balloon can result in damage to the lumen as well as failure to alleviate the stenosis. Non-limiting examples of compliant balloons are disclosed in U.S. Pat. No. 6,120,477 to Campbell et al. and U.S. Pat. No. 6,890,395 to Simhambhatla, each of which is incorporated by reference herein in its entirety. Additional examples are commonly known in the art.

It is not uncommon with either types of balloons to have some difficulty in properly positioning the balloon, which are usually located on the distal ends of catheters, within the region of the lesion of a patient's artery or other body lumen or, if properly positioned within the lesion, to have difficulty in maintaining the position of the inflatable member or balloon within the lesion during balloon inflation.

What is needed is a balloon which can be preferentially inflated in different sections to better control the position of the balloon and to provide a more uniform pressure against the lesion during the dilatation. In addition, there is a need for a balloon that can be preferentially inflated in different sections to more precisely expand an interventional device at the site of a lesion. Although U.S. Pat. Nos. 5,470,313 and 5,843,116 disclose focalized intraluminal balloons with variable inflation zones or regions, the present invention allows any type of balloon to be preferentially inflated at different sections without modifying the balloon or delivery catheter.

SUMMARY OF THE INVENTION

An aspect of the present invention relates to a medical device comprising an elongated tubular body with a proximal and distal end, at least one expandable element at the distal end of the elongated tubular body, and an expandable tubular sleeve surrounding at least a portion of the expandable element. The expandable tubular sleeve comprises at least two portions with differing radial strengths thereby influencing the shape of the expandable element and surrounding tubular sleeve and/or the amount of force required to expand the expanding element and/or surrounding tubular sleeve.

Another aspect of the present invention relates to a method of treating a site in a body lumen. The method comprises providing a medical device comprising an elongated tubular body with a proximal and distal end, at least one expandable element at the distal end of the elongated tubular body, and an expandable tubular sleeve surrounding at least a portion of the expandable element. The expandable tubular sleeve comprises at least two portions with differing radial strengths which influence the shape and/or force required to inflate the expandable element and/or surrounding expandable tubular sleeve. The medical device is positioned within a body lumen so that the expandable element in folded form is adjacent to a treatment site. The expandable element is then inflated at a pressure or force sufficient to inflate the expandable element at a first portion of the expandable tubular sleeve. If needed, the expandable element can be inflated at an increased pressure to inflate the expandable element at a second portion of the expandable tubular sleeve with greater radial strength than the first portion.

The operation of the present invention should become apparent from the following description when considered in conjunction with the accompanying drawings.

BRIEF DESCRIPTION OF THE FIGURES

FIG. 1 is a schematic illustration of an expandable element in expanded form of a medical device of the present invention.

FIG. 2 is a schematic illustration of an expanded element in folded form of a medical device of the present invention.

DETAILED DESCRIPTION OF THE INVENTION

Figure 3:
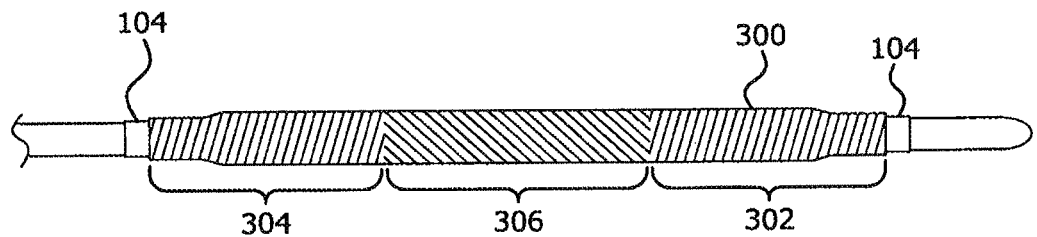
FIG. 3 is a schematic illustration of a medical device of the present invention with an expandable sleeve with regions of varying radial strengths covering the folded expandable element.

The present invention relates to medical devices with an expandable portion for insertion into the body lumen. More particularly, the present invention relates to balloon dilatation catheters for insertion in the vascular system. In one embodiment, the balloon dilatation catheter is a focal balloon dilatation catheter, meaning that expansive energy of the balloon is focused at one or more predetermined regions along the surface of the balloon.

Medical devices of the present invention comprise an elongated tubular body with a proximal and distal end, at least one expandable element at the distal end of the elongated tubular body, and an expandable tubular sleeve surrounding at least a portion of the expandable element.

One embodiment of the invention comprises a medical device comprising: an elongated tubular body with a proximal and distal end; (b) at least one expandable element at the distal end of the elongated tubular body; and (c) an expandable tubular sleeve surrounding at least a portion of the expandable element, said expandable tubular sleeve comprising at least two portions with differing compression ratios. In another embodiment, the expandable element is a balloon. In another embodiment, expandable element is self-expanding. In another embodiment, the expandable element is mechanically expanded. In another embodiment, the expandable element has a uniform thickness. In another embodiment, the expandable tubular sleeve has a uniform wall thickness after expansion. In another embodiment, the expandable tubular sleeve has a uniform wall thickness prior to expansion.

Elements of the medical device of the present invention are depicted in FIGS. 1 through 5.

Specifically, FIGS. 1 and 2 are illustrative of a general balloon catheter 100 having an elongated tubular body 102 with an expandable element 104.

The elongated tubular body 102 has a proximal control end 106 and a distal functional end 108. The balloon catheter also has a proximal guidewire lumen 110 that extends through the length of the elongated tubular body 102 and exits the distal end at a guide wire port 112. The balloon catheter shown is an "Over The Wire" configuration, as commonly known in the art. As an alternate, the catheter could have a mid-guidewire port and therefore have a "Rapid Exchange" configuration, as commonly known in the art. The balloon catheter 100 also incorporates a proximal inflation port 114 that allows fluid communication between the inflation port 114 and the inflatable element 104. The length and inner and outer diameter of the tubular body are selected based upon the desired application of the medical device. For example, in one nonlimiting embodiment, wherein the medical device is used in percutaneous transluminal coronary angioplasty, the length of the tubular body typically ranges from about 120 cm to about 140 cm. In this embodiment, the outer diameter of the tubular body ranges from about 0.026 inches to about 0.45 inches. As will be understood by the skilled artisan upon reading this disclosure, the length and/or diameter of the tubular body are in no way limiting and may be routinely modified for various applications of the medical devices of the present invention. The tubular body generally has a circular cross-sectional configuration. However, triangular and oval cross-sectional configurations can also be used.

The tubular body must have sufficient structural integrity to permit the medical device to be advanced to distal vascular locations without bending or buckling upon insertion. Various techniques are known for manufacturing the tubular bodies. In one embodiment, the tubular body is manufactured by extrusion of a biocompatible polymer.

In another embodiment, the present invention comprises a catheter, an expandable tubular sleeve, and an expandable member for expanding an interventional device, said expandable member preferentially inflated at different sections to better control the expansion of said implantable medical device. Non-limiting examples of said interventional devices are stents (which include stent-grafts), and heart valves.

FIG. 1 shows the expandable element 104 in expanded form while FIG. 2 shows the expandable element 104 in folded form.

Figure 4:
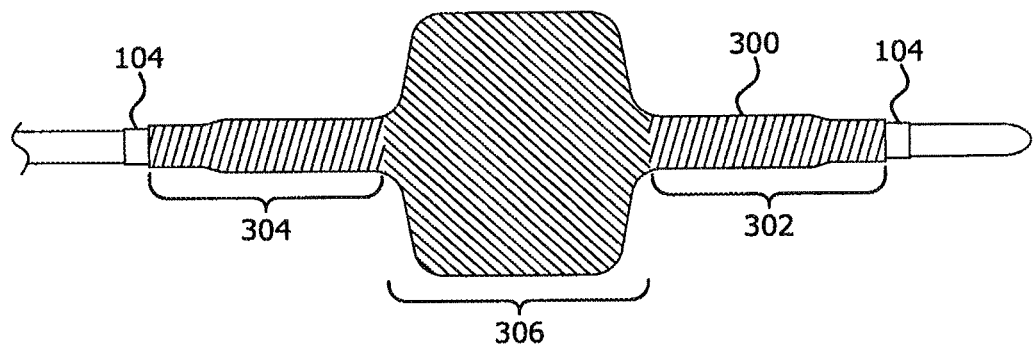
FIG. 4 is schematic illustration of a medical device of the present invention expanded at a first portion.
Figure 5:
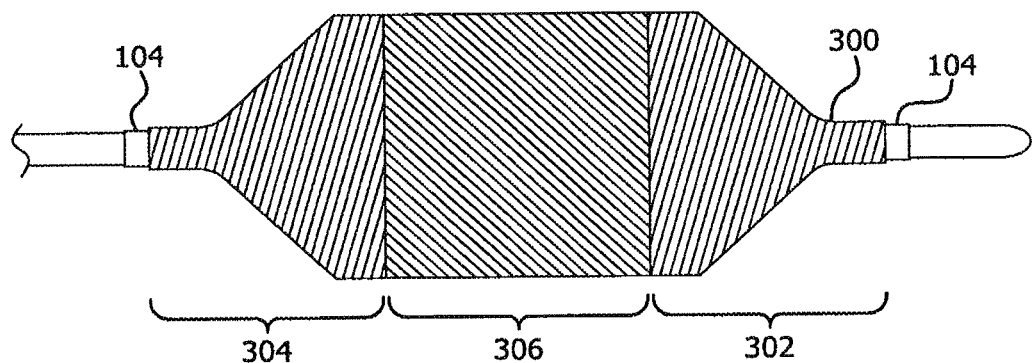
FIG. 5 is a schematic illustration of medical device of the present invention expanded in full at first and second portions.

As shown in FIGS. 3 through 5, the medical device of the present invention comprises an expandable tubular sleeve 300 surrounding at least a portion of the expandable element 104. The expandable tubular sleeve comprises one or more materials having a porous microstructure. Examples of suitable materials include, but are not limited to expanded polytetrafluoroethylene (ePTFE) and ultra high molecular weight polyethylene (UHMW PE). Thus, in one embodiment, the expandable tubular sleeve comprises one or more materials having a porous microstructure. In another embodiment, the material is fibrillated. In another embodiment, the material comprises ePTFE. In another embodiment, the material is UHMW PE. In another embodiment, the expandable tubular sleeve is affixed to the expandable element.

The expandable tubular sleeve comprises at least two portions with differing radial strengths. In one embodiment, as depicted in FIGS. 3 through 5, the expandable tubular sleeve 300 comprises a distal end portion 302 and a proximal end portion 304 with increased radial strength as compared to a central or middle portion 306. In this embodiment, as depicted in FIG. 4, the central portion 306 inflates first under less expansion pressure while the distal end portion 302 and proximal end portion 304 expand second only under additional expansion pressure. In another embodiment, the differing radial strengths of the portions of the expandable sleeve influence the shape of the expandable element and surrounding tubular sleeve. In another embodiment, the differing radial strengths of the portions of the expandable sleeve influence the amount of force required to expand the sleeve.

The tubular expandable sleeve may comprise a single continuous material. In one embodiment, the single continuous material expandable sleeve is comprised of a polymer having a node and fibril micro-structure. Refer to U.S. Pat. No. 3,962,153, which is incorporated by reference herein in its entirety. A tube of such material can be placed onto a mandrel, longitudinally compressed and heat treated to preserve the compressed state. Refer to U.S. Pat. No. 5,308,664, which is incorporated by reference herein in its entirety. The amount of longitudinal compression dictates the amount of radial strength. More longitudinal compression results in a higher degree of radial strength (i.e. the higher compression ratio). A continuous tube can therefore have discrete zones with varying amounts of longitudinal compression (compression ratio) resulting in discrete zones of radial strength. The varied radial strengths will then dictate the inflation profiles (or sequence) of an expandable element.

A continuous tube having discrete zones of radial strength according to the present invention can incorporate varying wall thicknesses and cross-sectional profiles. For example a continuous tube can have a circular, oval, triangular, square, rectangular or polygon cross-sectional shape. The tube can also incorporate wall sections of varying thickness. Various cross-sectional profiles and various wall thicknesses can be combined along a single tube.

Continuous tubes having discrete zones of radial strength according to the present invention can also incorporate lubricious coatings, drug eluting coatings, anti-microbial coatings, visualization aids or other additions that enhance the device function.

Various "staged inflation" balloon profiles can be derived by the use of an expandable sleeve that has discrete zones of varying radial strength. For example, a sleeve may be configured to have a weak (or easy to expand) zone on one end of a balloon, combined with other zones of stronger radial strength. Such a balloon would initially inflate on the one end (at a first pressure) and then progressively inflate along the balloon length at higher pressures. A balloon can have 2, 3, 4, 5, 6, 7, 8, 9, 10 or more discrete zones of varying radial strength. The various discrete zones of radial strength can be arranged along the balloon in any desired order. The radial strength of the discrete zones may also be individually tailored to expand with any desired pressure. The discrete zones of radial strength can be combined with non-expandable zones or with zones of very low radial strength. Multiple sleeves having discrete zones of radial strength can be combined in a longitudinal or co-axial configuration. An expandable sleeve having discrete zones of varying radial strength can be positioned externally or internally to the expandable element.

In one embodiment, the tubular expandable sleeve comprises ePTFE. It may be desirable to modify the ePTFE used for the present invention by incorporating various additives with said ePTFE. Fillers can be incorporated in ePTFE by known methods, such as the methods taught by U.S. Pat. No. 5,879,794, to Korleski. Additives can also be imbibed into the ePTFE by known methods. Additives can also be coated on the ePTFE by known methods. Suitable additives include, for example, materials in particulate and/or fiber form and can be polymers, adhesives, elastomers, ceramics, metals, metalloids, carbon, and combinations thereof. Particularly useful additives include, for example, radiopaque materials, such as certain metals (e.g. barium alloys) and carbon. The additives can be used in combination with desired adhesive materials when incorporated with the polymer. It may also be desirable to metalize the ePTFE or at least a portion thereof. An additive may be included in the matrix of the polymer itself, or contained within the voids defined by the polymeric structure, or both. Desirable fillers may also include colorants, medicaments, anti-microbials, antivirals, antibiotics, antibacterial agents, anti-inflammatory agents, anti-proliferative agents, anti-coagulating agents, hemostatic agents, analgesics, elastomers and mixtures thereof. Compounds which lubricate an ePTFE cover, thus allowing the material to slide smoothly across another material, can be used to coat, fill, or imbibe the tubular cover. Solid lubricants (i.e. graphite, waxes, silicone), fluid lubricants (i.e. hydrocarbon oils, silicone oils), gels (i.e. hydrogel) or any other biocompatible material known in the art may be used. In one embodiment, said expandable sleeve is coated, filled or imbibed on only one side. In another embodiment, said expandable sleeve is coated, filled or imbibed on both sides. In another embodiment, said expandable sleeve is coated, filled or imbibed on only one side and coated, filled or imbibed one the other side with a different material.

An expandable sleeve having discrete zones of radial strength, can dictate the expansion profile or sequence of an underlying (or overlying) expandable element. The controlled expansion profile or expansion sequence can be used to enable or improve various medical and industrial applications. For example, stents that are easily longitudinally compressed during expansion can be expanded by the balloon and cover of the present invention. Said stent can be expanded from the center out, thus maintaining the stent longitudinally tensioned as it is expanded. An example of such a stent is described in U.S. Patent Application Publication U.S. 2009/0182413, incorporated by reference herein for all purposes. The longitudinal tension prevents the stent from being longitudinally compressed. In an opposite configuration the balloon and cover can expand from the ends in towards the center and thereby compress the overlaying device. A heart valve stent may require a stent that is expanded in a specific "hour-glass" shape, wherein the hour-glass shape is developed in a specific sequence. In other applications the expansion can begin at one end and progress to the opposing end of the expansible element, thereby creating a "pushing" or peristaltic motion. In one embodiment, said stents can comprise 316L stainless steel, cobalt-chromium-nickel-molybdenum-iron alloy ("cobalt-chromium"), other cobalt alloys such as L605, tantalum, Nitinol, or other bio-compatible metals. In another embodiment, the stent can be a self expanding stent, a balloon expandable stent or a combination thereof.

In one embodiment, the thickness of the sleeve wall is selected to have a uniform wall thickness prior to expansion In another embodiment, the thickness of the sleeve wall is selected to have a uniform wall thickness after expansion. In another embodiment, the thickness of the sleeve wall is selected to have a uniform wall thickness prior to and after expansion.

The expandable tubular sleeve may be affixed to the expandable element or may be slidably positioned around the expandable element without a separate affixation means.

As shown in FIGS. 1 and 2, at least one expandable element 104 is provided at the distal end of the tubular body. An example of an expandable element useful in the present invention is an inflation balloon. Other forms of expandable elements include, but are not limited to mechanical expanders such as "Chinese Lanterns", expandable bow-arms, rotationally expandable/contractible coil springs, cam-type sliding mechanisms, expandable linkages, expandable collets, polymeric or natural materials that expand when activated and other configurations as commonly known in the art. The expandable element used in the medical device of the present invention may also be self-expanding (eliminated mechanically expand). In one embodiment, the expandable element has an outer wall of uniform thickness. The wall thickness can range from less than about 0.01 mm to about 5 mm. A typical 3 mm diameter thin walled noncompliant balloon can have a wall thickness of about 0.02 mm.

The balloon members according to the present invention may be formed from using any materials known to those of skill in the art. Commonly employed materials include the thermoplastic elastomeric and non-elastomeric polymers and the thermosets including the moisture curable polymers. Examples of suitable materials include but are not limited to, polyolefins, polyesters, polyurethanes, polyamides, polyimides, polycarbonates, polyphenylene sulfides, polyphenylene oxides, polyethers, silicones, polycarbonates, styrenic polymers, copolymers thereof, and mixtures thereof. Some of these classes are available both as thermosets and as thermoplastic polymers. See U.S. Pat. No. 5,500,181, for example. As used herein, the term copolymer shall be used to refer to any polymeric material formed from more than one monomer.

As used herein, the term "copolymer" shall be used to refer to any polymer formed from two or more monomers, e.g. 2, 3, 4, 5 and so on and so forth.

Useful polyamides include, but are not limited to, nylon 12, nylon 11, nylon 9, nylon 6/9 and nylon 6/6. The use of such materials is described in U.S. Pat. No. 4,906,244, for example.

Examples of some copolymers of such materials include the polyether-block-amides, available from Elf Atochem North America in Philadelphia, Pa. under the tradename of PEBAX®. Another suitable copolymer is a polyetheresteramide.

Suitable polyester copolymers, include, for example, polyethyelene terephthalate and polybutylene terephthalate, polyester ethers and polyester elastomer copolymers such as those available from DuPont in Wilmington, Del. under the tradename of HYTREL®.

Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether.

Specific examples of polyester/polyether block copolymers are poly(butylene terephthalate)-block-poly(tetramethylene oxide) polymers such as ARNITEL® EM 740, available from DSM Engineering Plastics and HYTREL® polymers available from DuPont de Nemours & Co, already mentioned above.

Suitable materials which can be employed in balloon formation are further described in, for example, U.S. Pat. Nos. 6,406,457; 6,284,333; 6,171,278; 6,146,356; 5,951,941; 5,830,182; 5,556,383; 5,447,497; 5,403,340; 5,348,538; and 5,330,428.

The above materials are intended for illustrative purposes only, and not as a limitation on the scope of the present invention. Suitable polymeric materials available for use are vast and too numerous to be listed herein and are known to those of ordinary skill in the art.

Balloon formation may be carried out in any conventional manner using known extrusion, injection molding and other molding techniques. Typically, there are three major steps in the process which include extruding a tubular preform, molding the balloon and annealing the balloon. Depending on the balloon material employed, the preform may be axially stretched before it is blown. Techniques for balloon formation are described in U.S. Pat. No. 4,490,421, RE32,983, RE33,561 and U.S. Pat. No. 5,348,538.

The expandable element may be attached to the tubular body by various bonding means known to the skilled artisan. Examples include, but are not limited to, solvent bonding, thermal adhesive bonding and heat shrinking or sealing. The selection of the bonding technique is dependent upon the materials from which the expandable element and tubular body are prepared. Refer to U.S. Pat. No. 7,048,713 to Wang, which is incorporated by reference herein in its entirety, for general teachings relating to the bonding of a balloon to a catheter.

Medical devices of the present invention are useful in treating sites in a body lumen or delivering interventional devices as described above. In one embodiment, the medical device of the present invention is used in angioplasty procedure. In this method, the medical device of the present invention is percutaneously advanced so that the expandable element in folded form is adjacent to a vascular treatment site. Generally the treatment site is a stenosis caused, for example, by plaque or a thrombus. The expandable element of the medical device is then inflated at a pressure or force sufficient to inflate the expandable element. After the stenosis is compressed to or beyond the native diameter of the lumen, the expandable element is evacuated and the medical device is withdrawn from the body lumen. In another embodiment, said medical devices of the present invention are useful for delivering an interventional device to a treatment site.

One embodiment of the invention comprises a method of treating a site in a body lumen, said method comprising the steps of positioning within a body lumen the medical device of the invention so that the expandable element in folded form is adjacent to a treatment site; and inflating the expandable element at a pressure or force sufficient to inflate the expandable element and to expand the expandable tubular sleeve according to its varying radial strength, as described above. In one embodiment, said expandable element expands an interventional device. In another embodiment, said interventional device is a stent. In another embodiment, said interventional device is a heart valve. In another embodiment, said treatment site is a coronary artery.

The following nonlimiting examples are provided to further illustrate the present invention.

Example 1

A film tube was placed over a folded PET balloon. The film tube had discrete zones having different amounts of radial strength, imparted by varying amounts of longitudinal compression. The middle zone of the film tube was longitudinally compressed 35%. The ends of the film tube were longitudinally compressed 60%. The resulting balloon inflated first in the middle zone when a first pressure was applied to the balloon. The ends of the balloon inflated when a second, higher pressure was applied to the balloon. The following example details a method of making a particular "staged inflation" balloon.

An ePTFE film was helically wrapped around a mandrel having a diameter of about 28.5 mm and a length of about 37 cm. The film width was about 2.54 cm. Two passes of film were wrapped in opposing directions, using a 2.794 mm pitch (measured from adjacent film edges) with a film angle of about 78°. The wrapped length was about 30 cm.

The film wrapped mandrel was then placed into an air convection oven heated to about 380° C. for about 28 minutes. This heat exposure bonded the layers of ePTFE, forming a thin film tube.

The ePTFE film wrapped mandrel was removed from the oven, allowed to cool, and the thin film tube was removed from the mandrel. The thin film tube had a diameter of about 28.5 mm and a wall thickness of about 0.0254 mm.

The about 30 cm long thin film tube and was then tensioned by hand and stretched longitudinally to about 400% of the original length, or to about 120 cm. After stretching, the tube was placed onto a mandrel having a diameter of about 4 mm and a length of about 130 cm. The stretched tube was smoothed by hand onto the mandrel, forming a small diameter thin film tube having a diameter of about 4 mm.

A temporary ePTFE film was then helically wrapped onto the about 4 mm diameter thin wall tube. The film thickness was about 0.00508 mm and the film width was about 1.905 cm. One pass of film was wrapped, using a 2.6924 mm pitch (measured from adjacent film edges) with a film angle of about 78°.

The thin film tube and temporary ePTFE film wrap was then longitudinally compressed. The middle portion of the thin film tube had an initial length of 33.75 mm and was compressed to a length of 25 mm. The first end of the thin film tube had an initial length of 44 mm and was compressed to a length of 27.5 mm. The second end of the thin film tube was longitudinally compressed in a similar manner to the first end of the thin film tube. The total length of the longitudinally compressed thin film tube was about 80 mm.

The longitudinally compressed thin film tube and mandrel was then placed into an air convection oven heated to about 380° C. for about 1 minute.

The ePTFE film wrapped mandrel was then removed from the oven and allowed to cool.

The temporary ePTFE film wrap was then removed from the thin film tube. The resulting thin film tube had discrete zones of varying radial strength.

Figure 6:
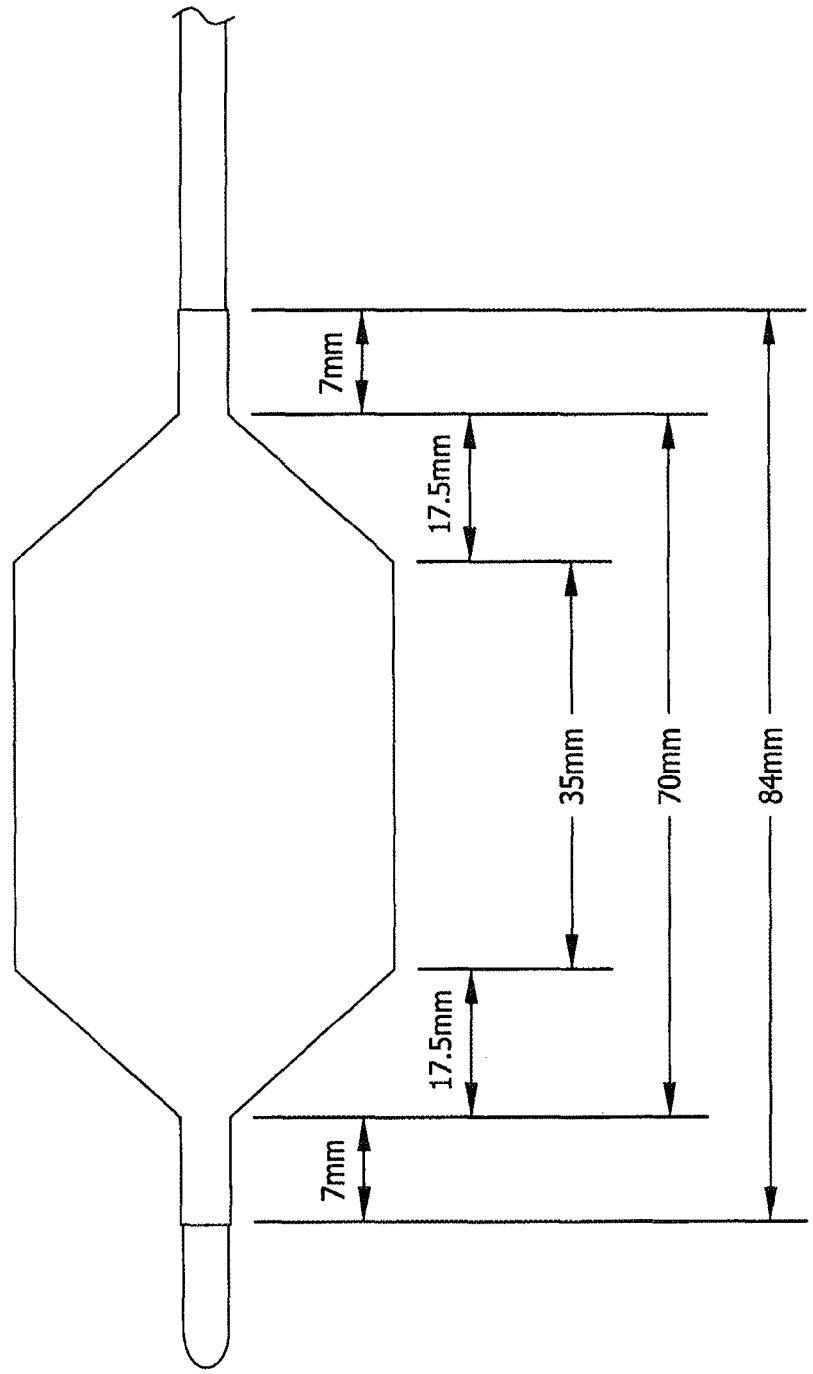
FIG. 6 is a side view of an expanded balloon showing typical dimensions.

The thin film tube was then placed over a catheter mounted, compacted PET balloon. The balloon is shown in an expanded state in FIG. 6. The thin film tube having discrete zones of radial strength was longitudinally centered onto the compacted balloon so that about 2 mm of the balloon legs protruded from the thin film tube. The ends of the thin film tube were secured to the balloon legs using 4981 Loctite Cyanoacrylate adhesive and 0.635 cm wide ePTFE film wrapped around both the thin film tube and the balloon leg.

The balloon was then pressurized to about 3 atm, inflating the center section of the balloon as depicted in FIG. 4. When further pressurized to about 12 atm, the proximal and distal ends of the balloon inflated as shown in FIG. 5.

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein. In addition to being directed to the embodiments described above and claimed below, the present invention is further directed to embodiments having different combinations of the features described above and claimed below. As such, the invention is also directed to other embodiments having any other possible combination of the dependent features claimed below.

What is claimed is:

1. A method of treating a site on a body lumen using a medical device, the method comprising:
    positioning within a body lumen the medical device so that an expandable element of the medical device when in a folded form is adjacent to a treatment site, the medical device including an expandable tubular sleeve coupled to the expandable element, the expandable tubular sleeve including a first portion having a first longitudinal compression of the expandable tubular sleeve resulting in a first radial strength and a second portion having a second longitudinal compression of the expandable tubular sleeve resulting in a second radial strength different from the first radial strength, the second portion located proximate the first portion;
    expanding the expandable element at a first pressure sufficient to expand the expandable element at the second portion of the expandable tubular sleeve according to a sequence of expansion dictated by the first and second radial strengths of the expandable tubular sleeve; and
    expanding the expandable element at a second increased pressure to expand the expandable element at the first portion of the expandable tubular sleeve according to the sequence of expansion.

2. The method of claim 1, further comprising: positioning the expandable tubular sleeve internally or externally to the expandable element.

3. The method of claim 1, wherein the expandable tubular sleeve has a uniform wall thickness prior to or after expansion.

4. The method of claim 1, wherein the first portion is a first end portion of the expandable tubular sleeve and the second portion is a middle portion of the expandable tubular sleeve.

5. The method of claim 4, the expandable tubular sleeve further including a second end portion which expands at the second increased pressure after the middle portion expands at the first pressure.

6. The method of claim 1, wherein the first portion is a middle portion of the expandable tubular sleeve and the second portion is a first end portion of the expandable tubular sleeve.

7. The method of claim 1, wherein the expandable tubular sleeve comprises one or more materials having a porous microstructure.

8. The method of claim 7, wherein the one or more materials includes expanded polytetrafluoroethylene.

9. The method of claim 7, wherein the one or more materials includes ultra high molecular weight polyethylene.

10. The method of claim 7, wherein the one or more materials includes a fibrillated material.

11. A method of treating a site on a body lumen using a medical device, the method comprising:
    positioning within a body lumen the medical device so that an expandable element in folded form is adjacent to a treatment site, the medical device comprising:
        an elongated tubular body having proximal and distal ends,
        the expandable element at the distal end of the elongated tubular body, and
        an expandable tubular sleeve including a first region having a first compression ratio and a second region having a second compression ratio different from the first compression ratio and disposed proximate the first region;
    expanding the expandable element at a pressure sufficient to expand the expandable element at the second region of the expandable tubular sleeve according to a sequence of expansion dictated by the first and second compression ratios; and
    expanding the expandable element at an increased pressure to expand the expandable element at the first region of the expandable tubular sleeve according to the sequence of expansion.

12. The method of claim 11, further comprising: positioning the expandable tubular sleeve internally or externally to the expandable element.

13. The method of claim 11, wherein the expandable tubular sleeve has a uniform wall thickness prior to or after expansion.

14. The method of claim 11, wherein the first region is an end region of the expandable tubular sleeve and the second region n is a middle region of the expandable tubular sleeve.

15. The method of claim 11, wherein the first region is a middle region of the expandable tubular sleeve and the second region is an end region of the expandable tubular sleeve.

16. A method of treating a site on a body lumen using a medical device, comprising:
    providing a medical device comprising:

an elongated tubular body having proximal and distal ends;

an expandable element at the distal end of the elongated tubular body; and an expandable tubular sleeve includes a first portion having a first longitudinal compression of the expandable tubular sleeve resulting in a first radial strength and a second portion having a second longitudinal compression of the expandable tubular sleeve resulting in a second radial strength different from the first radial strength;

positioning within a body lumen the medical device so that the expandable element in folded form is adjacent to a treatment site;

expanding the expandable element at a pressure sufficient to expand the expandable element at the first portion of the expandable tubular sleeve according to a sequence of expansion dictated by the first and second radial strengths of the expandable tubular sleeve; and expanding the expandable element at an increased pressure to expand the expandable element at the second portion of expandable tubular sleeve according to the sequence of expansion.

17. The method of claim 16, further comprising withdrawing the medical device from the body lumen after expanding the expandable element.

18. The method of claim 16, wherein the first portion of the expandable tubular sleeve comprises a central or middle portion of the expandable tubular sleeve and wherein the second portion of the expandable tubular sleeve comprises at least one of a distal end portion and a proximal end portion of the expandable tubular sleeve.

19. The method of claim 16, wherein the expandable tubular sleeve is positioned internally or externally to the expandable element.

* * * * *